US006656206B2

(12) United States Patent
Corcoran et al.

(10) Patent No.: US 6,656,206 B2
(45) Date of Patent: Dec. 2, 2003

(54) OCCLUSION DEVICE WITH NON-THROMBOGENIC PROPERTIES

(75) Inventors: Michael P. Corcoran, Woodbury, MN (US); Peter M. Buonomo, Shorewood, MN (US); Joseph A. Marino, Apple Valley, MN (US)

(73) Assignee: Cardia, Inc., Burnsville, MN (US)

( * ) Notice: Subject to any disclaimer, the term of this patent is extended or adjusted under 35 U.S.C. 154(b) by 9 days.

(21) Appl. No.: 10/055,460

(22) Filed: Jan. 23, 2002

(65) Prior Publication Data

US 2002/0068950 A1 Jun. 6, 2002

Related U.S. Application Data

(63) Continuation-in-part of application No. 09/311,508, filed on May 13, 1999.

(51) Int. Cl.$^7$ ................................................ A61B 17/08
(52) U.S. Cl. ...................................... 606/213; 606/151
(58) Field of Search .................................. 606/153, 157, 606/152, 154, 155, 213, 215; 623/2.42

(56) References Cited

U.S. PATENT DOCUMENTS

| | | | | |
|---|---|---|---|---|
| 3,673,612 A | * | 7/1972 | Merril et al. ............... | 623/2.42 |
| 3,874,388 A | * | 4/1975 | King et al. .................. | 606/232 |
| 4,917,089 A | * | 4/1990 | Sideris ........................ | 606/215 |
| 5,108,420 A | | 4/1992 | Marks ......................... | 606/213 |
| 5,171,259 A | | 12/1992 | Inoue .......................... | 606/213 |
| 5,284,488 A | | 2/1994 | Sideris ........................ | 606/213 |
| 5,334,217 A | * | 8/1994 | Das ............................. | 606/213 |
| 5,425,744 A | * | 6/1995 | Fagan et al. ................. | 606/213 |
| 5,433,727 A | | 7/1995 | Sideris ........................ | 606/213 |
| 5,451,235 A | | 9/1995 | Lock et al. .................. | 606/213 |
| 5,634,936 A | | 6/1997 | Linden et al. ............... | 606/213 |
| 5,649,950 A | * | 7/1997 | Bourne et al. .............. | 606/194 |
| 5,702,421 A | | 12/1997 | Schneidt ..................... | 606/213 |
| 5,709,707 A | * | 1/1998 | Lock et al. .................. | 606/213 |
| 5,725,552 A | | 3/1998 | Kotula et al. ................ | 606/213 |
| 5,741,297 A | | 4/1998 | Simon .......................... | 606/213 |
| 6,174,322 B1 | | 1/2001 | Schneidt ..................... | 606/213 |

OTHER PUBLICATIONS

Goosen et al., Inactivations of Thrombin by Anti Throbin III on a Heparinized Bio Material, Journal 20 (5–6) 1980, 543–544.
Merrill, Pilot Model of Artificial Kidney: Amino Acid Metabolism in Uremia of Man, Journal GRAI740; 1972.

* cited by examiner

*Primary Examiner*—Pedro Philogene
(74) *Attorney, Agent, or Firm*—Kinney & Lange, P.A.

(57) ABSTRACT

A method of forming a PVA foam structure for use in an occlusion device such that the PVA foam structure comprises non-thrombogenic properties. The method comprises forming a PVA gel and incorporating heparin into the PVA gel. The PVA foam structure is then treated with the PVA gel and heparin mixture, such as by soaking the PVA foam structure in the gel.

33 Claims, 7 Drawing Sheets

OCCLUSION DEVICE WITH NON-THROMBOGENIC PROPERTIES

CROSS-REFERENCE TO RELATED APPLICATION(S)

This is a Continuation in Part of U.S. patent application Ser. No. 09/311,508 filed on May 13, 1999, and invented by Michael Corcoran, Peter Buonomo, and Joseph Marino.

BACKGROUND OF THE INVENTION

This invention relates to an occlusion device for the closure of physical anomalies like vascular or septal apertures, such as patent ductus arteriosus, patent foramen ovale, atrial septal defects, or ventricular septal defects. More specifically, this invention relates to a method of forming a polyvinyl alcohol (PVA) foam treated with heparin for use in occlusion devices. The resulting PVA foam structure minimizes blood clotting.

Normally, permanently repairing certain cardiac defects in adults and children requires open heart surgery, a risky, expensive, and painful procedure. To avoid the risks and discomfort associated with open heart surgery, modern occlusion devices have been developed are that small, implantable devices capable of being delivered to the heart through a catheter. Rather than surgery, a catheter inserted into a major blood vessel allows an occlusion device to be deployed by moving the device through the catheter. One method of inserting an occlusion device begins by using a guide catheter introduced through the femoral vein and lower vena cava and placed in the right ventricle of the heart. After passing through the defect in the atrial septum, the distal portion of the implant is forced out of the catheter and unfolded in the left atrium, much like unfolding an umbrella. The unfolded portion is drawn back against the septum due to the pre-tensioning of the fixation devices. Then, the proximal parts of the implant are likewise pushed out of the catheter and independently unfolded in the right atrium. The insertion forceps used to guide the occlusion device through the catheter are then separated from the center piece.

This procedure is performed in a cardiac cathlab and avoids the risks and pain associated with open heart surgery. These modem occlusion devices can repair patent foramen ovale, patent ductus arteriosis, atrial septal defects, ventricular septal defects, and other cardiac and non-cardiac apertures. One such device is that disclosed in PCT application PCT/US98/15961, entitled Occlusion Device for the Closure of a Physical Anomaly Such as a Vascular Aperture or an Aperture in a Septum, filed on Jul. 31, 1998 by Bernhard Schneidt, now issued U.S. Pat. No. 6,174,322. This patent discloses a non-thrombogenic occlusion device that is insertable into an anomaly via a catheter. In addition, a similar device filed as German Appln. 297 14 242.9 on Aug. 8, 1997, discloses an occlusion device which can be inserted via a catheter. Another devices is that disclosed in U.S. Pat. No. 6,206,907, entitled Occlusion Device with Stranded Wire Support Arms, filed on May 7, 1999, invented by Joseph A. Marino, Michael P. Corcoran, and Peter M. Buonomo.

There are several types of these new occlusion devices capable of being inserted via a catheter, including button devices, collapsible umbrella-like structures, and plug-like devices. One major draw back is that the intent of some of these occlusion devices is to stimulate thrombosis, or a blood clot. This stimulation of a blood clot (thrombosis) on the device creates one of the biggest concerns in closing a defect. Such a clot may lead to a stroke if the clot should pass from the right atrium to the left atrium, pass through to the left ventricle, through the aorta, and to the brain.

Thus, there is a significant need in the art for an occlusion device that will occlude septal defects and will minimize thrombosis occurring at the device.

BRIEF SUMMARY OF THE INVENTION

The present invention alleviates concerns with blood clots forming around an occlusion device used to close a physical anomaly, such as a patent foramen ovale. The present invention is an occlusion device for closure of a physical anomaly. The occlusion device is comprised of a center section, to which is attached upper and lower elastic shape memory fixation devices. Attached to the fixation devices are sheets (e.g. polyvinyl foam sheets) which serve to occlude the anomaly. The polyvinyl alcohol foam sheets are treated with heparin. Heparin minimizes or eliminates thrombosis formation and bonds well to polyvinyl alcohol foam. Because of the heparin, the chances of a blood clot forming at the occlusion device are reduced and almost eliminated.

To create the non-thrombogenic PVA foam structure, the PVA foam structure is treated with a PVA heparin gel. The PVA heparin gel comprises a PVA in a gel form having heparin bonded to the PVA. By soaking the PVA foam structure in the mixture of PVA and heparin, the PVA molecules of the foam structure may bond to the PVA molecules in the PVA heparin mixture. The PVA molecules in the mixture which bond with the PVA molecules in the foam also comprise heparin. As a result, the PVA foam structure has long lasting non-thrombogenic properties that do not dissipate or wash off.

A first PVA sheet is attached to the upper fixation devices and a second PVA sheet is attached to the lower fixation device. The shape of the foam sheets can be a square, a circle, or any other such suitable shape. The sheet on the upper fixation device may be oriented asymmetrically from the sheet on the lower fixation device. This is advantageous in that a wider variety of anomalies can be closed using such an arrangement, including anomalies of different sizes and shapes.

Once attached to the center section, the fixation devices and the attached foam sheets are collapsible so that the entire occlusion device can be moved through a catheter. The fixation devices hold the occlusion device in place once it is inserted into an aperture. To prevent any damage to surrounding tissue, the fixation devices are fitted with atraumatic tips. In addition, the fixation devices have a shape memory, which allows the fixation devices to return to their original shape, or "remember" their shape even after being bent or deformed for passage through a catheter. In setting the shape, the deformation caused by passage through a catheter is taken into account.

DETAILED DESCRIPTION

Figure 1:
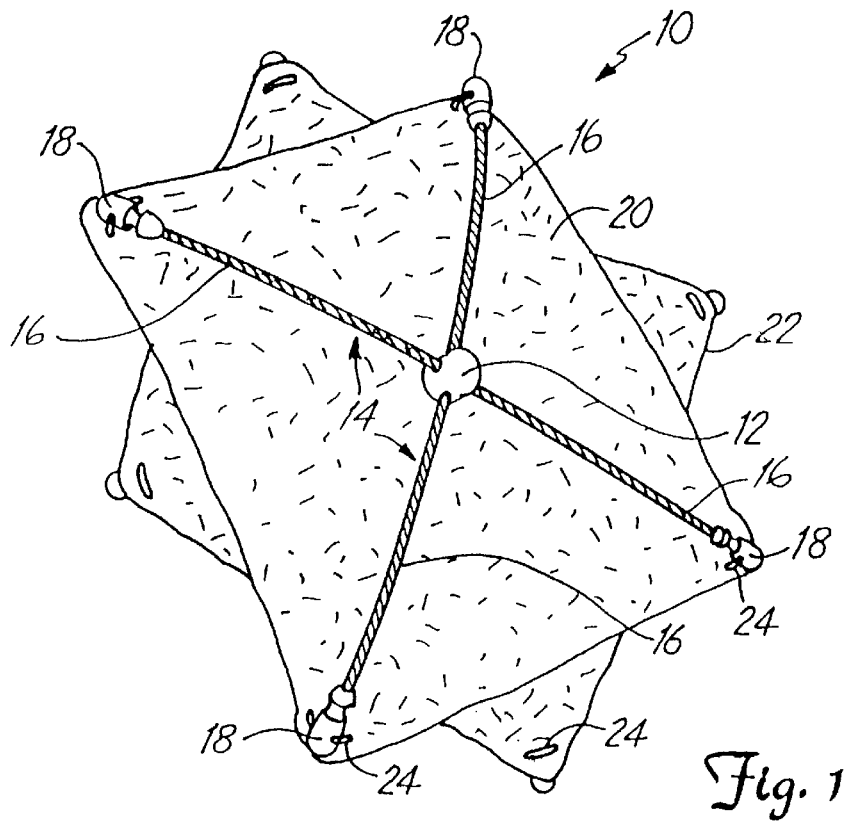
FIG. 1 is a top perspective view of an occlusion device with stranded wire support arms.

FIG. 1 is a top perspective view of an occlusion device. The occlusion device 10 is comprised of a center section 12 extending in the axial direction. The center section 12 has attached an upper stranded wire elastic shape memory fixation device 14 comprising four upper stranded wire arms 16. Attached to the end of each stranded wire arm 16 is an atraumatic tip 18. Most notably, the occlusion device 10 comprises a first sheet 20 attached to the atraumatic tips 18 via a sutures 24. Also visible is the second sheet 22.

Figure 2:
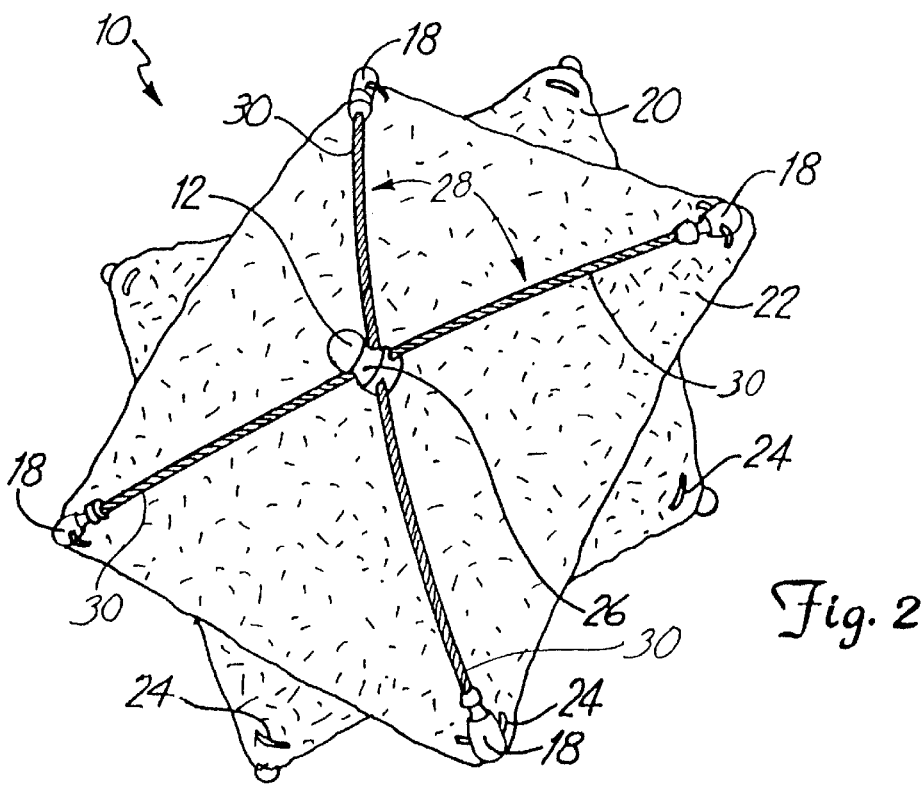
FIG. 2 is a bottom perspective view of an occlusion device with stranded wire support arms.

FIG. 2 is a bottom view of the same occlusion device 10 more clearly showing second sheet 22. Also visible in FIG. 2 is the bottom of the center section 12 with a groove 26. Attached through the bottom of center section 12 is the lower stranded wire elastic shape memory fixation device 28 comprising four bottom stranded wire arms 30. Once again, the wire arms 30 are capped with atraumatic tips 18. The second sheet 22 is attached to the lower stranded wire elastic shape memory fixation device 28 via sutures 24 sewn through the tips 18.

The sheets 20, 22 are comprised of a medical grade polymer in the form of film, foam, gel, or a combination thereof. Preferably, a high density polyvinyl alcohol (PVA) foam is used, such as that offered under the trade name IVALON®. To minimize the chance of the occlusion device 10 causing a blood clot, the foam sheets 20, 22 are treated with a thrombosis inhibiting material. One such suitable material is heparin.

Heparin has the ability to keep blood from clotting and is used chiefly in the prevention and treatment of thrombosis. Heparin is an extended polymer of repeating sugar units that requires an intact three dimensional structure to express its biological activity. A particularly critical region of the heparin molecule is the highly specific "active sequence" of five sugar residues that bind to and accelerate the activity of antithrombin, the most important inhibitor of the enzymes that control clotting of blood. Heparin bonds extremely well to PVA foam. Once the foam sheets 20, 22 are treated with heparin, the chances of a blood clot forming around the occlusion device 10 are significantly reduced and nearly eliminated.

There are several options for treating the PVA foam with heparin. First, the PVA foam is sliced into sheets of a desired size and thickness. Next, the sheets are dipped in a heparin solution for a predetermined amount of time at the desired temperature, and then the foam sheets are removed and allowed to dry. Dipping the sheets in heparin results in a coating of heparin which is not very permanent. The heparin slowly wears off the sheets, creating a localized area of thrombosis inhibition. Eventually the heparin completely dissipates leaving little if any of the desirable non-thrombogenic properties.

Another option for treating PVA foam with heparin is to alter the surface of the foam to provide a better chance of the heparin attaching to the foam sheets. The foam sheets may be plasma etched, or may undergo a similar surface treatment to either roughen the surface of the foam or polarize the molecules so that the surface is more receptive to the heparin. Once the surface has been treated, the foam is once again dipped in a heparin solution. The heparin solution may or may not also contain a chemical to enhance the ability of the heparin to stick to the foam sheets. When applied this way, the heparin and its effects last longer, though there may still be some dissipation of the heparin.

Yet another method of applying heparin to PVA foam is to do so on the molecular level. Rather than dipping the foam in heparin, the heparin is added when the foam is formed so that a permanent bond is created when a heparin molecule bonds to a PVA molecule. In such a process, heparin is incorporated into the PVA foam during the manufacturing process by adding heparin to a liquid PVA solution. During the bonding process, catalysts, heat, or other methods of enhancing the reaction maybe used in connection with the liquid PVA and heparin mixture. This mixture of PVA and heparin is then processed to create a foam. Because the heparin is permanently bonded to the PVA foam, the effects of the heparin are virtually permanent and little or no dissipation occurs.

Still another method of forming a foam structure for use in an occlusion device so that the foam structure has non-thrombogenic properties is to soak the foam structure in a mixture of PVA and heparin. Because heparin bonds well with PVA, the mixture of PVA and heparin contains heparin bonded to PVA molecules. Like molecules bond with like molecules so that once the PVA foam structure is soaked in the mixture of PVA and heparin, the PVA molecules of the foam structure may bond to the PVA molecules in the PVA heparin mixture. The PVA molecules in the mixture which bond with the PVA molecules in the foam also comprise heparin. As a result, after being coated with the PVA heparin mixture, the PVA foam structure has long lasting non-thrombogenic properties that do not dissipate or wash off.

The mixture of PVA and heparin applied to the PVA foam structure is preferably a gel. The viscosity of the PVA heparin gel is preferably thin enough to allow the PVA foam structure to become coated with the gel. If the PVA heparin gel is too thick, the gel simply sits on top of the foam structure and does not suitably coat the structure. A PVA heparin gel having a viscosity similar to syrup works well.

One method of forming a suitable PVA heparin gel is to first form the PVA gel. PVA can be obtained in powdered form. In forming the PVA gel, powdered PVA is mixed with water until the PVA dissolves into solution. A small amount of heat can be applied to assist the PVA in dissolving. Once the PVA gel is made, the heparin is added. To assist the heparin in bonding to the PVA, heat and other chemicals may be used.

One suitable method for incorporating heparin into a PVA gel is as follows. To form the PVA gel, 7 grams of PVA powder are added to 150 ml of water. The mixture is heated to about 90° C. The mixture is removed from heat, and 4 grams of glycerol are added. The mixture is returned to the heat, and is stirred while reducing the heat to about half the present temperature. After stirring for about three to five minutes, eight grams of formaldehyde are added. The mixture is returned to heat, stirred for three to five minutes, removed from heat, and 2 grams of heparin are added. After adding the heparin, the mixture returned to heat and is stirred for about ten minutes. Next, the mixture is removed from heat, about 10.5 grams of $MgCl_2*6H_2O$ are added, and the mixture is stirred for about ten minutes. The mixture is once again removed from heat, and four grams of glutaraldehyde are added. The mixture is returned to heat and is stirred for about ten minutes. Finally, 25 ml of water are added, and the mixture is stirred for about another 15 minutes.

Once the PVA heparin gel is formed, the PVA foam structures can be placed in the PVA heparin gel to coat the foam structures. It may be preferable to cool the PVA heparin gel mixture before doing so for ease of handling. The foam structures are soaked in the PVA heparin gel long enough to allow the PVA molecules in the PVA heparin gel to bond to the PVA molecules of the foam. Soaking for about five minutes is often a suitable length of time. After the PVA foam structures have been soaked in the PVA heparin gel, the structures are removed and rinsed with buffered saline. The rinse serves to clean the foam structures, stop the chemical reactions, and remove any unreacted chemicals from the foam structures.

PVA foam comes in a variety of grades, which correlate to the porosity of the PVA foam. In forming the foam sheets 20, 22, the grade of PVA foam used may be any grade of foam having the desired properties for use in occluding a defect. Because the PVA foam is porous, the PVA heparin gel penetrates into the foam sheets 20,22 beyond just the surface of the sheets 20, 22. As a result, the non-thrombogenic properties caused by the PVA heparin gel coated foam sheets are long lasting, do not dissipate, and are highly effective.

PVA foam structures, such as foam sheets 20, 22, may be obtained by cutting the sheets from a block of PVA foam. Once cut, the sheets 20, 22 are then soaked in the PVA heparin gel to give the sheets 20, 22 the desired non-thrombogenic properties. Alternatively, because of the porosity of the PVA foam, a small block of PVA foam may be soaked in a PVA heparin gel. After the PVA foam has been soaked in the gel, the foam structures, such as sheets 20, 22, can be cut from the treated block of PVA foam.

In addition to treating sheets 20, 22 of PVA foam, PVA heparin gel can be used to treat other PVA foam structures as well. For instance, it may be desirable to treat the foam plug 122 (FIG. 9), or any other part of an occlusion device which is formed of PVA foam. Further, the same method of forming a foam structure having long lasting non-thrombogenic properties may be used in connection with other foam structures used in other types of occlusion devices. Thus, the present method is not limited to foam sheets 20, 22.

The PVA foam sheets 20, 22 have a thickness when dry between about 0.2 mm and 2.0 mm. Preferably, the thickness of the foam sheets 20, 22 when dry is between about 0.3 mm and about 0.8 mm. PVA foam sheets 20,22 are preferably formed to these thicknesses by slicing thin sheets of foam from a thicker foam block. When the foam sheets 20, 22 are generally square, the sheets 20, 22 preferably have a diagonal dimension of between about 5 mm and about 50 mm. Preferably, the diagonal dimension is between about 18 mm and about 30 mm. After exposure to blood or other moisture, the PVA foam sheets 20, 22 expand on the order of about 10% in thickness.

An important advantage of the present invention is that the PVA foam sheets 20, 22 immediately block blood flow as soon as they are unfolded during implantation. The physician therefore can test the effectiveness of the occlusion device 10 immediately after placement by injecting x-ray contrast fluid through the catheter. If the occlusion device 10 is for any reason not positioned so that it is properly blocking the aperture, the physician can use the forceps to reposition or remove the occlusion device 10. In contrast, prior art devices using DACRON® do not initially block blood flow, but rather require clotting to take place in the DACRON® over a period of days or weeks. This "residual shunting" makes it much more difficult to ascertain whether an effective deployment of an occlusion device has occurred.

Another advantage is that PVA foam may be formulated in a radiopaque form, which allows the physician to see the device more clearly during deployment. This ensures proper positioning of the device 10. In addition, PVA foam is a proven bio-compatible material. The cellular nature of PVA foam promotes rapid endothelialization. The PVA foam sheets 20, 22 will expand considerably when wetted. The softness and expandability allow the PVA foam sheets 20, 22 to expand and conform as needed to occlude or fill a defect. This is particularly advantageous because current techniques for determining the size and shape of septal defects are not precise.

PVA foam can be shaped in a wide variety of sizes and configurations. It is easily handled and worked in its dry, rigid state, yet is soft and highly compressible after it has been wetted. This permits the fabrication of devices of a wide variety of shapes, both simple and complex. For example, device 10 can be custom formed to fit a particular patient's defect. Likewise, though the preferred embodiment shown has the sheet shaped as a square, it is also possible for this sheet to be shaped in a circle or other suitable shape.

The occlusion device 10 is constructed so that the upper and lower wire elastic shape memory fixation devices 14, 28 are easily collapsible about the center section 12. Due to this construction, the occlusion device 10 can be folded so that the upper wire elastic shape memory fixation device 14 is folded upwards in the axial direction and the lower wire elastic shape memory fixation 28 device is folded downwards in the axial direction. The first and second sheets 20, 22 attached to the upper and lower elastic shape memory fixation devices 14, 28 are flexible and likewise collapse as the upper and lower fixation devices 14, 28 are folded.

Figure 3:
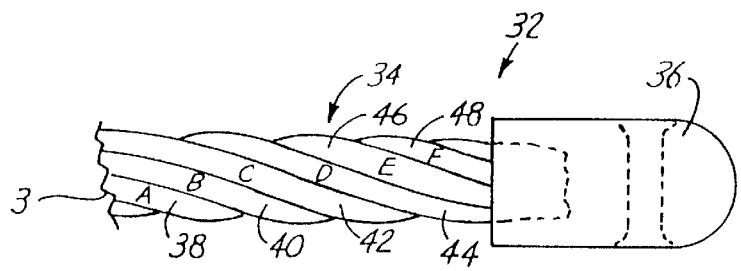
FIG. 3 is a greatly enlarged side view of a portion of the stranded wire support arm and atraumatic tip.

A human heart pulses up to 5 billion times over its lifetime. In the past, occlusion devices have suffered from fatigue failures, such as cracks or breaks, due to the extreme environment the human heart poses. To avoid these fatigue failures, one embodiment of the present invention relies on making the fixation devices 14, 28 out of stranded wires or cables. FIG. 3 is a greatly enlarged detail of a portion of the stranded wire shape memory fixation device 32. Visible is multi-wire strand 34 comprised of a 1×7 strand. The 1×7 strand is comprised of six individual wires, 38–48 laid bout a center wire (not shown). An atraumatic tip 36 caps the strand 34 and serves to prevent potential unraveling of the strand 34 while at the same time preventing damage to surrounding tissue. Each wire 38–48 of the multi-wire strand 34 is made of a suitable material capable of shape memory, such as a nickel-titanium alloy, commonly called Nitinol. Nitinol is preferably used because it is commercially available, very elastic, non-corrosive, and has a fatigue life greater than that of stainless steel. Nitinol is known to those skilled in the art.

The multi-wire strand 34 has been subjected to a precise pre-shaping to give it a "shape memory". This pre-shaping can be done by means of machining or heat treatment or both. The shape memory helps to hold the strands together, prevent unraveling, and can be used to add pre-tension to the wire so that the wires can return to (or remember) their shape even after the strong deformation that occurs when the occlusion device is passed through a catheter.

Of particular benefit to the invention is the significant extension of cycle life the multi-wire strand 34 adds to the fixation devices. While an individual wire, when subjected to the repeated pulsings of a human heart, may likely suffer a fatigue failure and either fracture or break, a multi-wire strand greatly decreases the chances of such a failure. The reason being that when formed in a strand or a cable, the resulting cycle life of the strand or the cable approximates the cycle life of each individual wire. Small diameter wires have the greatest resistance to fatigue failure, and thus have the longest cycle life, because they are extremely elastic. However, this elasticity also means that the small diameter wires do not have enough stiffness to perform the function required of the fixation device, that is to occlude an anomaly and hold the device in place. When stranded, the small diameter wires retain the elasticity and resistance to fatigue failure, and yet also obtain the necessary stiffness required to allow the device to function. Thus, the resulting strand benefits from significantly increasing its cycle life while not greatly increasing in size. There are several options for either strands or cables to be used in the present invention.

Figure 4:
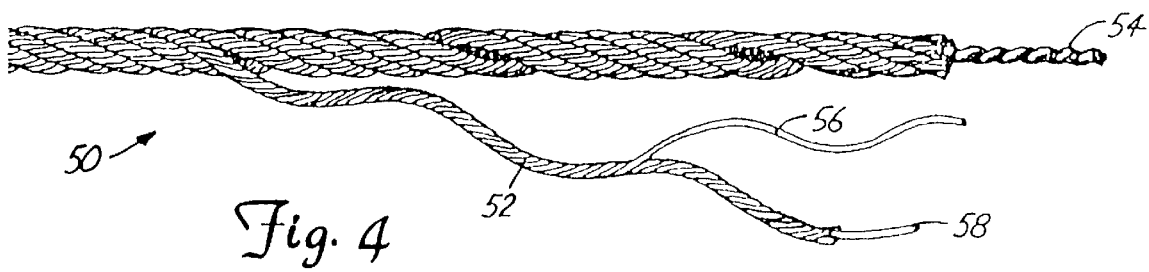
FIG. 4 is a perspective view of a cable comprised of wire strands.

A cable refers to two or more strands laid together, and a strand refers to two or more wires laid together. FIG. 4 is a perspective view of a multi-wire cable 50. The cable 50 is made of several strands 52 laid about a core 54. Each strand 52 is made of several individual wires 56 laid about a center 58. Also visible in FIG. 4 is the lay of the cable, which is a right regular lay. The lay refers to the direction, length, and general pattern that the wires 56 are laid in strand 52 and the strands 52 are laid in cable 50.

A left lay is when the wire 56 or strands 52 are laid in a helix having a left-hand pitch, similar to a left hand screw. Similarly, a right lay is when the wire 56 or strands 52 are laid in a helix having a right-hand pitch, similar to a right hand screw. Regular lay refers to cable 50 in which the wires 56 in the strands 52, and the strands 52 in the cable 50 are laid in opposite directions. A regular lay is standard, affording good flexibility and kink resistance. A lang lay refers to a cable 50 in which the wires 56 in the strands 52 and the strands 52 in the cable 50 are laid in the same direction. A lang lay is more flexible than the regular lay, but is also more susceptible to kinks. In addition, the lang lay cable, should only be used in applications where the cable 50 is not allowed to turn, or the cable 50 will unwind itself.

The length of the lay also provides information regarding the cable or strand. The length of the lay is the distance, in a straight line, in which a wire will make one complete spiral around the strand's center core, or in the case of a cable, the distance in which a strand will make one complete spiral around the cable's core. Generally, the longer the lay, the stronger the strand or cable, and the shorter the lay, the more flexible the strand or cable. Good combinations of flexibility and strength can be obtained by using a length of lay factor of 10 times the finished strand diameter for strand, and 7 times the finished cable diameter for cable.

Figure 5:
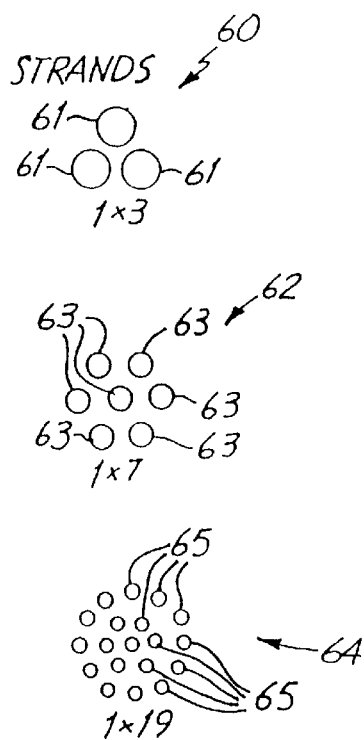
FIG. 5 is a graphical illustration of wire strands.

A variety of strand options are illustrated in FIG. 5. The construction of a strand is normally referred to as 1× the number of wires involved. Thus, a 1×3 strand 60 comprises three wires 61 laid together. Similarly, a 1×7 strand 62 comprises six wires 63 laid about a single wire. Likewise, a 1×19 strand 64 comprises a 1×7 strand with twelve wires 65 laid about it. The 1×3 strand 60 is the simplest construction of a strand with symmetrical balance. The 1×3 strand 60 is very flexible when the individual wires 61 have extremely small diameters. The 1×7 strand 62 is stronger than the 1×3 strand 60, but has essentially the same flexibility range. A 1×7 strand 62 is more symmetrical in configuration and affords better flexibility when made of small diameter wires 63. The 1×19 strand 64 is likewise stronger than a 1×7 strand 62 and more symmetrical in configuration, affording still better properties as far as flexibility and strength than the 1×7 strand 62. Because the fatigue resistance and cycle life of a strand approximates the fatigue resistance and cycle life of each individual wire, it is possible to use much smaller diameter wires to achieve a desired cycle life, while keeping the outer diameter of the strand within a desired size.

Any of the options shown in FIG. 5 can be used in connection with the present invention. Preferably, the individual wires 61, 63, 65 used to form either a 1×3, 1×7, or 1×19 strand 60, 62, 64 have a diameter of less than 0.008 inch, more preferably the wires 61, 63, 65 have a diameter of less than 0.005 inch. At this size, the outer diameter of the strand can be kept within a desired diameter, but a significant increase in cycle life is gained. For instance, using 0.005 inch wires 63 in a 1×7 strand 62 results in the outer diameter of the strand 62 being 0.015 inch (because the strand is three wires 63 across). This 0.015 inch diameter strand has significantly more resistance to fatigue than a solid 0.015 inch diameter wire would, yet retains many of the desirable properties, such as flexibility, as a 0.005 inch wire. When 0.001 inch wires 63 are used in a 1×7 strand 62, the resulting outer diameter is 0.003 inches.

When using a 1×19 strand 64, the outer diameter is five times the diameter of the individual wires 65 used (because the strand is five wires 65 across). Thus, if 0.005 inch wires 65 are used, the outer diameter becomes 0.025 inch. If 0.001 inch diameter wires 65 are used, the outer diameter of the strand 64 is 0.005 inch.

However, it is not necessary for all wires in the strand to have the same diameters. For instance, a 1×7 strand 62 comprises six wires 63 laid about a center. The center wire 63 can have a diameter different from the six wires 63 laid about it. For example, the diameter of the center wire may be 0.001 inch and the diameters of the outer wires may be 0.005 inch. Further, the center wire 63 may be made of a strand of wires rather than being a solid wire. Similarly, in a 1×19 strand 64, twelve wires 65 are laid about a 1×7 strand center. The twelve wires 65 laid about the center can have a different diameter than the wires 65 used to make the 1×7 strand center.

Figure 6:
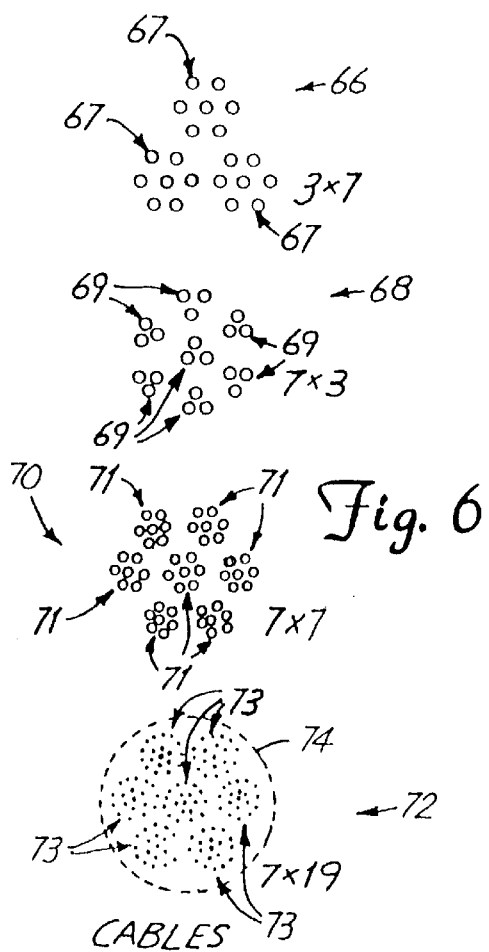
FIG. 6 is a graphical representation of cables.

FIG. 6 illustrates several configurations of cable. As mentioned above, a cable is two or more strands laid together. The construction of a cable is normally referred to as the number of strands × number of wires in each strand. For instance, a 3×7 cable 66 is a combination of three 1×7 strands 67. A 3×7 cable 66 is very flexible when made with small diameter wires. A 7×3 cable 68 is a combination of seven 1×3 strands 69, and has properties essentially the same as a 3×7 cable 66, but results in a much smoother strand. A 7×7 cable 70 is a combination of seven 1×7 strands 71, which allows for abrasion resistance and flexibility through a wide range of wire diameters. A 7×19 cable 72 is a combination of seven 1×19 strands 73 producing a combination of strength and very good flexibility.

With any of the cables or strands, it is possible to coat the cable or strand, as illustrated by the 7×19 cable 72 with a coating 74. Much like the benefits of strands, the benefits of a cable are increased strength. The strength of a cable is about 83% of the aggregate strength of each individual wire. Thus, it is possible to use a much smaller diameter wire to create a cable of a desired diameter, strength, and flexibility.

Cables, much like strands, are suitable for use in connection with the present invention. Varying configurations of cable can be used, including 3×7, 7×3, 7×7, 7×19, or any other suitable configuration. Most preferably, the diameter of the cable used in the present invention is less than about 0.025 inch. The cable may be laid on either a solid core or laid about a core comprised of multiple wires or strands of wires.

Though discussed in terms of cables and strands, stranded wire may also refer to other configurations of wires. For instance, stranded wire also includes braided or woven wire. Further, stranded wire may simply be several individual wires laid together, affixed at points along the length of the wires to keep the bundle together.

Figure 7:
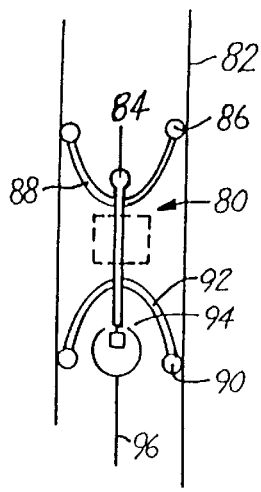
FIG. 7 is a side diagrammatic view of the occlusion device inserted into a catheter.

The occlusion device must be foldable so that it can be inserted into a catheter for implantation in or retrieval from a patient. FIG. 7 is a side diagrammatic view of an occlusion device 80 inserted into a catheter 82. The center section 84 extends in the vertical direction. Attached to the center section 84 is the upper stranded wire elastic shape memory fixation device 86 to which a first heparin treated sheet 88 is attached. The upper stranded wire elastic shape memory fixation device 86 and first sheet 88 are folded upwards in such a way as to fit inside the catheter 82. Likewise, the lower stranded wire elastic shape memory fixation device 90 and the second heparin treated sheet 92 attached thereto are folded downwards to fit inside the catheter 82.

Visible once again on the center section 84 is groove 94. The center section 84, also referred to as a center strut or center piece, preferably has an axial length of about 20 mm or less. In particular, center section 84 preferably has a length between about 1 mm and about 10 mm. Though shown as having a solid center section 84, the center section 84 may be articulated or constructed of stranded wire so that it is flexible.

Having a flexible center section 84 is advantageous because often when implanted, an occlusion device may be located in an irregularly shaped anomaly. Having a flexible center section 84 allows the occlusion device 80 to fit in a wider variety of anomalies, despite the shape or size of the anomaly. For instance, one side of the anomaly may be only a few millimeters thick, but another side may be many more millimeters thick. In such cases, one side of the occluding device 80 may be bent open further than the other side, putting more stress on the fixation device 86, 90 used on that side. If the center section 84 is flexible, the center section 84 can bend such that the upper or lower fixation device 86, 90 need not be the only location where the occlusion device adjusts to fit the anomaly.

The groove 94 allows for a guide forceps 96 to manipulate the occlusion device 80 as it is pushed through the catheter 82. Likewise, the guide forceps 96 can be used to position the occlusion device 80 once it reaches the desired location or be used to retrieve the device 80 should it not be placed properly. The groove 94 may additionally have a cross-sectional area which allows a forceps 96 to rotatably move the device 80 while the device is inserted into an anomaly. The groove 94 is grasped by a forceps 96 so that there is at least some play between the forceps 96 and the groove 94 when pushing the device 80 through a catheter 82. In particular, the guide forceps 96 engages the groove 94 by means of a claw-like or hook-like end.

Because the relative movement between the forceps 96 and the device 80 results in a relatively short rigid unit, the occlusion device 80 can be passed through sharply curved positions. In addition, because the device 80 is foldable, it can easily be retrieved if deployed or implanted imperfectly simply by grasping any part of the device 80. Because the stranded wire fixation devices are so flexible, grasping one part of a fixation device 86, 90 and pulling on it will cause the remaining portions of the device 80 to be folded in the axial direction along the center section 84 so that the device 80 can be removed.

Due to the small diameter of catheter 82, the upper and lower fixation devices 86, 90 undergo a strong deformation which can have an adverse effect on an implanted occlusion device 80 by causing the ends of the fixation devices 86, 90 to retain some of the deformation caused by being folded, and thus project away from the septal wall after insertion. For this reason, the upper and lower stranded wire elastic shape memory fixation devices 86, 90 are formed of stranded wire that has been formed by mechanical means and heat treated to retain its shape or "remember" its configuration.

Figure 8:
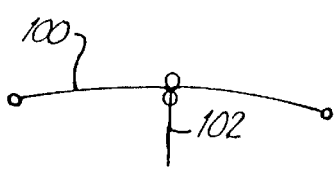
FIG. 8 is a side diagrammatic view of a stranded wire elastic shape memory fixation device.
Figure 8A:
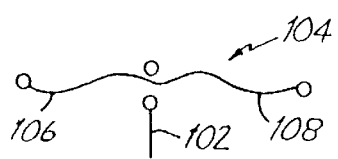
FIG. 8A is a side view of an alternate embodiment of an stranded wire elastic shape memory fixation device.

One reason for giving the fixation devices 86, 90 a shape memory is to prevent any unraveling of the individual strands. But more importantly, the shape memory ensures that the fixation devices 86, 90 will hold the PVA foam 88, 92 sheets next to the walls of the area to be occluded. Thus, the pre-shaping takes the form of a convex curve which urges the fixation devices 86, 90 toward the septum wall. FIG. 8 is one illustration of a suitable configuration for the shape memory of the fixation devices. Shown is a first multi-wire strand arm 100 threaded through the center section 102. The holding arms 100 need not necessarily lay flat against a vascular wall. As shown, the arms 100 are curved to form a convex shape. In this way, the desired contact with the septal wall takes place. In addition, other suitable shapes are possible as illustrated in FIG. 8A. In FIG. 8A, one holding arm 104 is divided into two legs 106, 108 in which each leg raises as it emanates from the center piece 102 only to slope downwards after reaching a maximum. In this manner, the desired contact with the wall of the area to be occluded still takes place.

Figure 9:
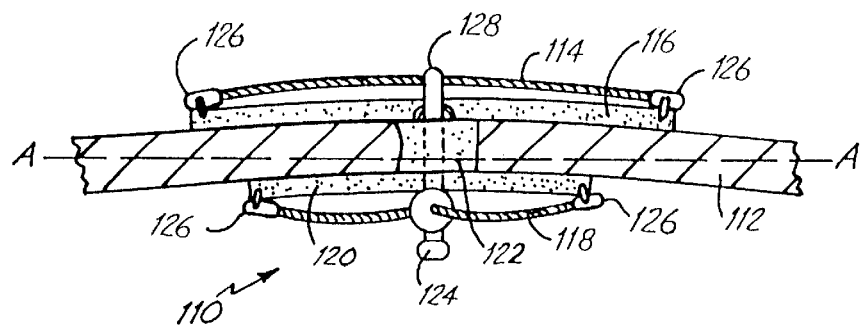
FIG. 9 is a side diagrammatic view of an occlusion device inserted into septal anomaly.

The shape memory feature is further illustrated in FIG. 9, which is a side view of an occlusion device inserted into a septal anomaly. The occlusion device 110 is used to close an occlusion in the septal wall 112. In doing so, the upper stranded wire fixation device 114 is used to hold the first heparin treated foam sheet 116 essentially flush against the septal wall 112. In like manner, the lower stranded wire fixation device 118 is used to hold the second heparin treated foam sheet 120 essentially flush against the other side of the septal wall 112. Also shown in FIG. 9, is an optional heparin treated foam plug 122 which further serves to fill the occlusion or septal anomaly. As mentioned before, the stranded wire fixation devices 114, 118 are formed so that they are pre-shaped or pre-tensioned. Due to this pre-tensioning or pre-shaping, the fixation devices 114, 118 urge the attached sheets 116, 118 toward the septal wall 112. In this manner, the occlusion device 110 is held securely against both sides of the septal wall 112.

Also shown in FIG. 9 are atraumatic tips 126, which are affixed to the ends of the fixation devices 114, 118. The center section 124 is also fitted with an atraumatic tip 128. The atraumatic tips 124, 128 ensure that there is a minimum of tissue damage caused by the occlusion device 110 when inserted.

Figure 10:
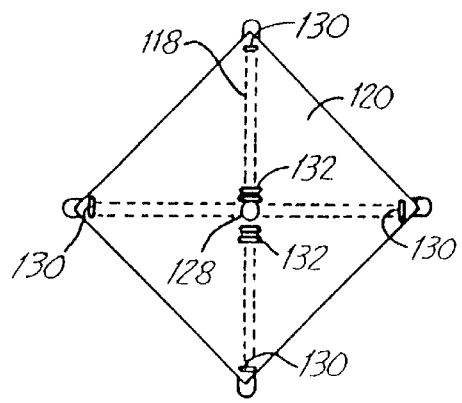
FIG. 10 is a bottom view of a portion of the occlusion device taken along line A.

FIG. 10 is a view taken along line A in FIG. 9 showing a bottom view of second heparin treated sheet 120. As evidenced in FIG. 10, the second heparin treated sheet 120 is attached to the fixation device 118 via sutures 130. Likewise, the second heparin treated sheet 120 is attached to the center section 128 via sutures 132. Though described as being attached via sutures 130, 132, the sheet 120 can also be attached by cementing, joining to, or molding over the fixation device 118 in other suitable manners. The sheet 120 is comprised of a medical grade polymer in the form of film, foam, gel, or a combination thereof, that has been treated with heparin to reduce the chances of thrombosis. Preferably, a material is used which is offered under the trade name IVALON® and is a high density foam.

Figure 11:
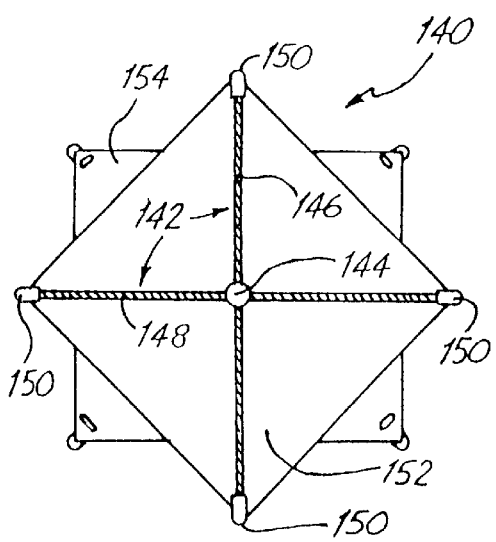
FIG. 11 is a top view of the occlusion device with stranded wire support arms.

The occlusion device 110 may be used in a variety of physical anomalies of a variety of sizes and shapes. To accomplish this, the device 110 is comprised of two parts that are offset from one another by 45°. FIG. 11 is a top plan view of the occlusion device 140 with an upper stranded wire elastic shape memory fixation device 142. Visible is the center section 144 through which the fixation device 142 extends. The fixation device 142 comprising a first multi-wire strand shape memory arm 146 and a second multi-wire strand shape memory arm 148. Attached to the arms 142, 146 is a first sheet 152. A second sheet 154 is placed asymmetrically below first sheet 152, offset by 45°. This asymmetric configuration allows for more precise insertion of the occlusion device 140. Likewise, the asymmetric configuration allows for the occlusion device 140 to be used in a wider variety of anomalies, such as those with irregular shapes. At the end of each arm 142, 146, are atraumatic tips 150.

Figure 12:
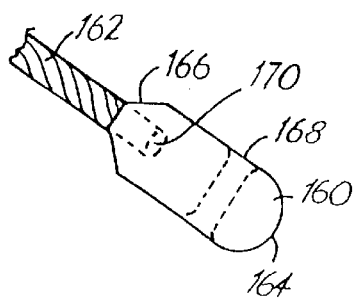
FIG. 12 is an enlarged view of a portion of the stranded wire elastic shape memory arm and atraumatic tip.

FIG. 12 offers a greatly enlarged view of an atraumatic tip 160 attached to a multi-wire strand shape memory fixation device 162. The tip 160 can be joined with the fixation device 162 by pressing, welding, or cementing. The tip 160 is a molded, elongated metal body having a rounded distal end 164 and a beveled proximal end 166. The tip 160 also has a hole drilled 168 into which a filament can be passed through to join the tip 160 to a PVA foam sheet. Blind hole 170 in the proximal end 166 of tip 160 receives the distal end of multi-wire strand 162.

The atraumatic tip 160 shown in FIG. 12 is particularly advantageous because its elongated shape makes it easy to crimp the tip 160 onto the distal end of the multi-wire strand 162. The elongated shape also makes its easier to drill a hole 168 through the tip 160. However, such a tip 160 can be made from a spherical object as well. The bevel of the proximal end 166 is also important in that it provides a smooth surface when pulling the device into a guide catheter or introducer. With other embodiments of atraumatic tips, a more abrupt junction between the tip 160 and wire strand 162 can cause the device to hang up on that junction when the occlusion device is being loading into a catheter.

Figure 13:
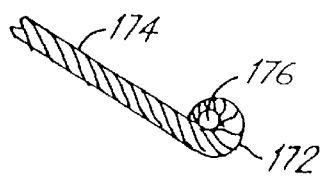
FIG. 13 is an alternate embodiment of an atraumatic tip formed from a stranded wire elastic shape memory arm.

FIG. 13 shows another embodiment of an atraumatic tip 172 located at the end of the multi-wire strand 174. In FIG. 13, the atraumatic tip 172 is formed at the end of a multi-wire strand 174 by rounding and polishing the strand 174 at its distal end. Tip 172 is circular, and includes an aperture 176 through which a filament can be extended for suturing a PVA foam sheet to the tip 172.

Figure 14:
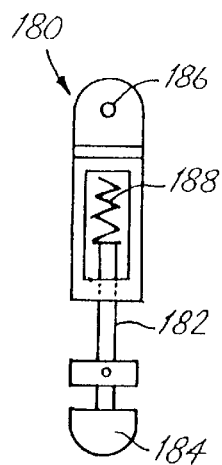
FIG. 14 shows a side view of a center piece of an occlusion device.

FIG. 14 is a side view of one embodiment of center section 180. The center section 180 may be made from ceramic, plastic, or metals (such as platinum, iridium, titanium) or combination thereof. Center section 180 has a center bridge 182, a contacting piece 184, and a head piece 186. The contacting piece 184 with the center bridge 182 can be telescopically pushed toward headpiece 186 in order to easily adapt to different septal or vessel wall thicknesses. Thus, center bridge 182 is supported in relation to head piece 186 by means of spring 188. Other well known adjustable options for varying the length of center section 180 may also be used, or center section 180 may be of a fixed length.

Figure 15:
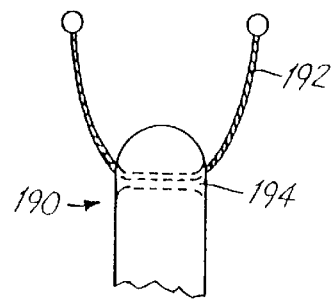
FIG. 15 shows a detail of a center piece of an occlusion device.

FIG. 15 is a side view of a detail of a center section 190. As mentioned, the elastic shape memory fixation device 192 passes through the center section 190 and the fixation device 192 is capable of being deformed in the axial direction. In order to ensure that the fixation device 192 is not kinked or severed by a sharp edge, any holes 194 used for the fixation device 192 are rounded off. Thus, when the fixation device 192 passes through the hole 194 and is strongly deformed, it is much less likely to be sheared off or permanently kinked since the edges of the hole 194 are beveled or rounded off. Another benefit of the beveled hole 194 is that the fixation device 192 can be bent in closer proximity to the center section 190, thus allowing the use of a smaller diameter catheter. Such a configuration occurs on holes 197 on both the center section 190, and also on any holes drilled in the atraumatic tips to allow sutures to pass there through. In this manner, it can be assured that the suture thread will not be sheared off by a sharp edge.

Figure 16:
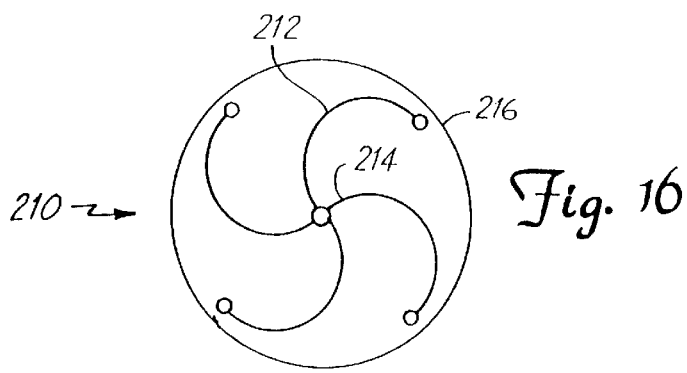
FIG. 16 is a top view of one embodiment of the occlusion device wherein the elastic shape memory fixation devices are shaped in an "S" form.
Figure 17:
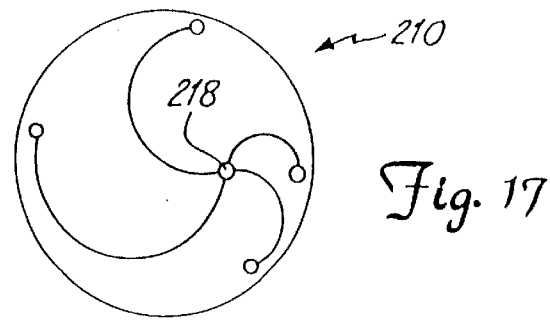
FIG. 17 is a top view of one embodiment of the occlusion device wherein the elastic shape memory fixation devices are not centered about the sheets.

FIG. 16 shows an alternate embodiment of an occlusion device 210. The device 210 is configured with holding arms 212 and 214, which rather than being formed straight, are shaped in the form of an "S" and are bent in such a way that the arms 212, 214 are enclosed by a circle 216 in the form of an envelope. The free ends of the holding arms 212, 214 are located within the respective envelope 216. The advantage of such a configuration is that in the event of forces acting from outside the holding arms 212, 214 which, for instance, can occur with the shrinkage of a heart upon aging, the free ends will not lead to injuries of the septa. FIG. 17 illustrates another configuration with an off center arrangement. In FIG. 17, the center section 218 is not located in the center of the device 210. This configuration makes it possible to close septal defects of irregular shape.

Though discussed in terms of support arms, the multiple wire strands and cables are suitable for use with other embodiments of occlusion devices. The stranded wire design may replace any stainless steel single wire occlusion device designs, including those utilizing hinges or coils. One such device that would benefit from stranded wire is U.S. Pat. No. 5,451,235, Occluder and Method for Repair of Cardiac and Vascular Defects. The multiple wire stands and cables are also suitable for use with collapsible frame configurations of occlusion devices.

Figure 18:
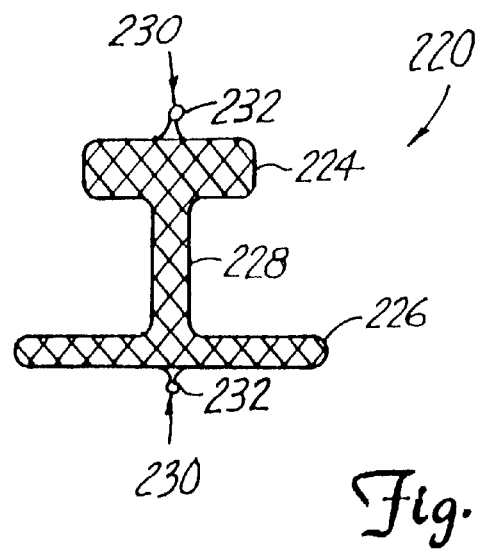
FIG. 18 is a side view of a collapsible frame occlusion device.
Figure 19:
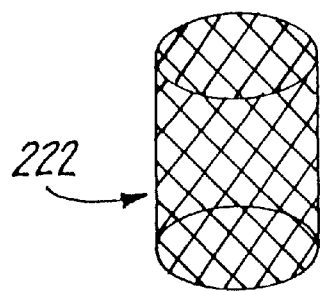
FIG. 19 is a side view of a mesh type fabric constructed of multiple wire strands or cable.

FIG. 18 is a side view of a collapsible frame occlusion device 220 comprised of a multiple wire strand mesh fabric type material. The material, more fully illustrated in FIG. 19, is comprised of several wire strands or cables interwoven to form a hollow tube-like structure 222. As shown in FIG. 18, the mesh can be formed into an occlusion device 220 with a first collapsible frame 224 and a second collapsible frame 226 separated by a center section 228.

In creating the device 220, the mesh is formed into the desired shape, either through use of a mold or other suitable method, and heat treating the wires to give them a "shape memory". In this manner, even after being elongated to move through a catheter, the device 220 will return to its preformed shape once inserted into an anomaly. Though the present embodiment shows the first frame 224 as being smaller than the second frame 226, the frames 224, 226 can be the same size. In the present embodiment, the larger frame 226 is placed on the side of the septum against which the most pressure is exerted. The smaller frame 224 serves to hold the device 220 in place.

Because the mesh material may unravel, the ends 230 of the device 220 are crimped to hold the material together. The crimped area 230 can be topped with atraumatic tips 232. Due to the device 220 being made of the collapsible mesh, the device 220 can be elongated in the axial direction and stretched into a narrow tube capable of being loaded into a catheter. The tips 232 may be configured so that a forceps can be engaged to guide the device 220 through the catheter for implantation. To further aid in occluding a septal defect, the device 220 may have fiber inserted into the mesh. Likewise, a PVA foam sheet treated with heparin can be attached to the collapsible frames 224, 226 to aid in occlusion.

Though discussed in terms of a collapsible occlusion device, heparin treated foam sheets may be used on many other types of occlusion devices, namely the button and plug type devices. Making button or plug type devices out of heparin treated PVA foam ensures that the risk of a blood clot forming around the device is reduced and almost eliminated.

Although the present invention has been described with reference to preferred embodiments, workers skilled in the art will recognize that changes may be made in form and detail without departing from the spirit and scope of the invention.

What is claimed is:

1. A method of creating a non-thrombogenic polyvinyl alcohol foam structure for use in an occlusion device, the method comprising:

forming a structure from polyvinyl alcohol foam;

applying a mixture comprising polyvinyl alcohol and heparin chemically bonded to the polyvinyl alcohol to the polyvinyl alcohol foam structure; and attaching the foam structure to an occlusion device.

2. The method of claim 1 wherein forming a structure from polyvinyl alcohol foam comprises cutting the polyvinyl alcohol foam to obtain a polyvinyl alcohol foam sheet.

3. The method of claim 1 wherein the mixture of polyvinyl alcohol and heparin chemically bonded to the polyvinyl alcohol comprises a gel.

4. The method of claim 3 and further comprising rinsing the polyvinyl alcohol foam structure after the structure has been soaked in the gel.

5. The method of claim 3 wherein applying the gel to the polyvinyl alcohol foam structure comprises soaking the foam structure in the gel for about five minutes.

6. A method of forming a polyvinyl alcohol foam structure having non-thrombogenic properties for use in an occlusion device, the method comprising:

creating a polyvinyl alcohol mixture comprising polyvinyl alcohol and heparin bonded to the polyvinyl alcohol;

applying the polyvinyl alcohol heparin mixture to the polyvinyl alcohol foam structure; and attaching the polyvinyl alcohol foam structure to an occlusion device.

7. The method of claim 6 wherein creating a polyvinyl alcohol mixture comprising polyvinyl alcohol and heparin bonded to the polyvinyl alcohol comprises:

creating a polyvinyl alcohol gel; and adding heparin to the polyvinyl alcohol gel.

8. The method of claim 7 wherein adding the heparin to the polyvinyl alcohol gel further comprising utilizing a catalyst to assist the heparin in bonding to the polyvinyl alcohol.

9. The method of claim 7 and further comprising applying heat to the polyvinyl alcohol gel to assist the heparin in bonding to the polyvinyl alcohol.

10. The method of claim 7 and further comprising obtaining a foam structure from a larger amount of polyvinyl alcohol foam.

11. The method of claim 10 wherein obtaining a foam structure comprises obtaining a sheet of polyvinyl alcohol foam from a block of polyvinyl alcohol foam.

12. The method of claim 11 wherein applying the polyvinyl alcohol gel to the polyvinyl alcohol foam structure comprises soaking the polyvinyl alcohol foam sheet in the polyvinyl alcohol gel.

13. The method of claim 12 wherein the polyvinyl alcohol foam sheet is soaked in the polyvinyl alcohol gel for about five minutes.

14. The method of claim 13 and further comprising rinsing the polyvinyl alcohol foam sheet after applying the polyvinyl alcohol gel to the foam sheet.

15. The method of claim 14 wherein rinsing the polyvinyl alcohol foam sheet comprises rinsing the foam sheet with buffered saline and allowing the sheet to dry.

16. An occlusion device comprising a polyvinyl alcohol foam structure having non-thrombogenic properties, the polyvinyl alcohol foam structure comprising:

a polyvinyl alcohol foam substrate;

a mixture comprising polyvinyl alcohol and heparin chemically bonded to the polyvinyl alcohol applied to the polyvinyl alcohol foam substrate.

17. The polyvinyl alcohol foam structure of claim 16 wherein the mixture comprises a polyvinyl alcohol heparin gel.

18. An occlusion device, the device comprising:

a center section extending in an axial direction;

upper and lower elastic shape memory fixation devices emanating from the center section; and first and second foam sheets attached to the upper and lower fixation devices, respectively, wherein the foam sheets are formed of polyvinyl alcohol foam which has been treated with a mixture comprising polyvinyl alcohol and heparin chemically bonded to the polyvinyl alcohol.

19. An occlusion device for the closure of a physical anomaly, the device comprising:

a support structure including a center section and first and second flexible arms extending outward from the center section; and a first foam sheet attached to the first flexible arm, wherein the first foam sheet is formed of polyvinyl alcohol foam which has been treated with a polyvinyl alcohol gel comprising polyvinyl alcohol and heparin chemically bonded to the polyvinyl alcohol.

20. The occlusion device in claim 19 and further comprising a second foam sheet attached to the second flexible arm, wherein the second foam sheet is formed of polyvinyl alcohol foam which has been treated with a polyvinyl alcohol gel comprising polyvinyl alcohol and heparin chemically bonded to the polyvinyl alcohol.

21. An occlusion device, the device comprising:
   a center strut;
   a first plurality of fixation devices extending from a first end of the center strut;
   a first sheet attached to the first plurality of fixation devices, wherein the first sheet is formed of polyvinyl alcohol foam which has been treated with a mixture comprising polyvinyl alcohol and heparin chemically bonded to the polyvinyl alcohol; and
   a second plurality of fixation devices extending from a second end of the center strut.

22. The occlusion device of claim 21 and further comprising a second sheet attached to the second plurality of fixation devices, wherein the second sheet is formed of polyvinyl alcohol foam which has been treated with a mixture comprising polyvinyl alcohol and heparin chemically bonded to the polyvinyl alcohol.

23. An occlusion device, the device comprising:
   a center strut having distal and proximal ends;
   a first set of stranded wire support arms extending from the distal end of the center strut;
   a first sheet attached to the first set of arms, wherein the first sheet is formed from polyvinyl alcohol foam which has been treated with a polyvinyl alcohol gel comprising polyvinyl alcohol and heparin chemically bonded to the polyvinyl alcohol;
   a second set of stranded wire support arms extending from the proximal end of the center strut; and
   a second sheet attached to the second set of support arms, wherein the second sheet is formed from polyvinyl alcohol foam which has been treated with a polyvinyl alcohol gel comprising polyvinyl alcohol and heparin chemically bonded to the polyvinyl alcohol.

24. An occlusion device for the closure of a physical anomaly, the occlusion device comprising:
   a center piece extending in an axial direction;
   first and second collapsible support frames spaced from one another and emanating from the center piece, the support frames being formed by multiwire strands; and
   first and second foam sheets attached to the first and second collapsible support frames, respectively, wherein the sheets are formed from polyvinyl alcohol foam which has been treated with a mixture comprising polyvinyl alcohol and heparin chemically bonded to the polyvinyl alcohol.

25. An occlusion device, the device comprising:
   a first collapsible support frame;
   a second collapsible support frame, the second collapsible support frame being spaced from and connected to the first collapsible support frame;
   a first sheet attached to the first collapsible support frame, wherein the first sheet is formed from polyvinyl alcohol foam which has been treated with a mixture comprising polyvinyl alcohol and heparin chemically bonded to the polyvinyl alcohol; and
   a second polyvinyl alcohol sheet attached to the second collapsible support frame, wherein the second sheet is formed from polyvinyl alcohol foam which has been treated with a mixture comprising polyvinyl alcohol and heparin chemically bonded to the polyvinyl alcohol.

26. An occlusion device, the device comprising:
   a support structure; and
   a polyvinyl alcohol foam occlusion member attached to the support structure wherein the occlusion member is formed from polyvinyl alcohol foam which has been treated with a mixture comprising polyvinyl alcohol and heparin chemically bonded to the polyvinyl alcohol.

27. A method of creating foam sheets for use in an occlusion device wherein the foam sheets have non-thrombogenic properties, the method comprising:
   providing polyvinyl alcohol foam;
   slicing the foam into sheets of a desired size;
   dipping the foam sheets into a solution comprising a thrombosis inhibitor; and
   attaching the foam sheets to an occlusion device.

28. The method of claim 27 wherein the thrombosis inhibitor is heparin.

29. The method of claim 27 wherein the solution comprises a chemical fixative to aid in keeping the heparin on the foam sheets.

30. The method of claim 27 and further comprising preparing a surface of the foam sheets to accept the heparin.

31. The method of claim 30 wherein preparing the surface of the foam sheets comprises plasma etching the surfaces of the foam sheets.

32. A method of creating foam with non-thrombogenic properties for use in an occlusion device, the method comprising:
   forming a mixture of polyvinyl alcohol and heparin in a liquid state;
   forming a foam of the polyvinyl alcohol and heparin mixture; and
   attaching the foam to an occlusion device.

33. The method of claim 32 and further comprising slicing the foam into sheets 18.

* * * * *

UNITED STATES PATENT AND TRADEMARK OFFICE
CERTIFICATE OF CORRECTION

PATENT NO. : 6,656,206 B2 Page 1 of 1
DATED : December 2, 2003
INVENTOR(S) : Michael P. Corcoran et al.

It is certified that error appears in the above-identified patent and that said Letters Patent is hereby corrected as shown below:

<u>Column 1,</u>
Line 2, delete "modem" and insert -- modern --.

<u>Column 4,</u>
Line 38, delete "maybe" and insert -- may be --.

Signed and Sealed this

Twenty-fourth Day of February, 2004

JON W. DUDAS
*Acting Director of the United States Patent and Trademark Office*